Figure 1:
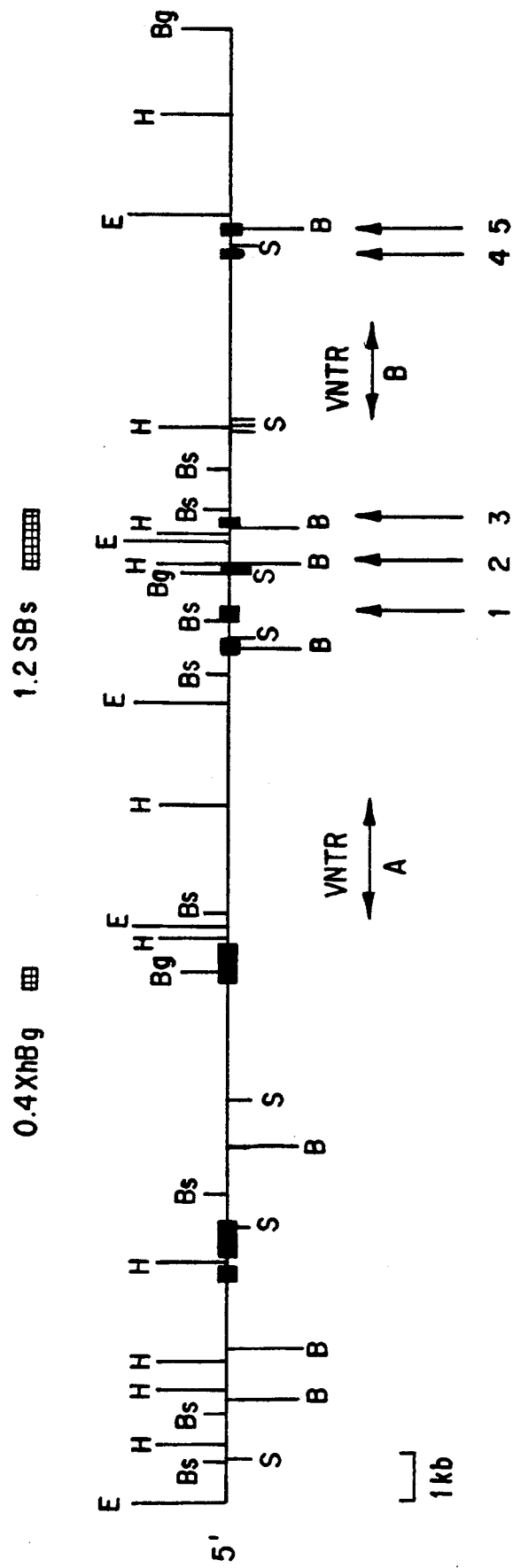

United States Patent [19]

Groffen et al.

[11] Patent Number: 5,273,878

[45] Date of Patent: Dec. 28, 1993

[54] NUCLEIC ACID PROBES THAT REVEAL HYPERVARIABLE RESTRICTION FRAGMENT LENGTH POLYMORPHISMS WITHIN THE ABR GENE

[76] Inventors: John Groffen; Nora Heisterkamp, both of 2321 W. Silverlake Dr., Los Angeles, Calif. 90039

[21] Appl. No.: 575,512

[22] Filed: Aug. 30, 1990

[51] Int. Cl.$^5$ .............................................. C12Q 1/68
[52] U.S. Cl. .................................. 435/6; 435/320.1; 436/501; 536/22.1; 536/23.1; 536/24.1; 536/24.2; 536/24.31; 536/24.32; 536/24.33; 935/17; 935/78
[58] Field of Search ............... 435/6, 91; 436/501; 536/27; 935/17, 78

[56] References Cited

FOREIGN PATENT DOCUMENTS

84/04758  12/1984  World Int. Prop. O. .
8602948   5/1986   World Int. Prop. O. .

OTHER PUBLICATIONS

Jeffreys et al. (1985) Nature, vol. 314, pp. 67–73.
Heisterkamp et al. (1989) Nucleic Acids Research, vol. 17, No. 21, pp. 8821–8831.
Sigma Chemical Co. Catalog, (1986), Sigma Chemical Co., St. Louis, Mo., p. 902.
Nakamura et al., 1987, Science, 235:1616–1622.
Jeffreys, 1986, "Hypervariable DNA and Genetic Fingerprints," Current Communications in Molecular Biology, pp. 57–61.
Frank, 1986, J. Theor. Biol. 122:303–309.
Wong et al., 1986, Nucleic Acids Research 14:4605–4616.

Primary Examiner—Margaret Moskowitz
Assistant Examiner—Ardin H. Marschel

[57] ABSTRACT

The present invention relates to nucleic aid molecules which comprise subfragments of ABR gene sequence. In particular embodiments, the nucleic acid molecules of the invention comprise portions of nucleic acid sequence contained in plasmids pVNTR-A or pVNTR-B. The invention is based, in part, on the discovery that a Taq-1 fragment of pVNTR-B, an EcoRI/HindIII fragment of pVNTR-A and, in preferred embodiments, a combination of these two fragments may be used to demonstrate restriction fragment length polymorphisms in the DNA of human subjects. Such restriction fragment length polymorphisms may provide a "genetic fingerprint" which may be used to identify individual persons or to provide evidence of a filial relationship in paternity cases. The nucleic acid sequences of the invention offer the advantage of producing an easily readable pattern in restriction fragment polymorphism analysis.

15 Claims, 3 Drawing Sheets

NUCLEIC ACID PROBES THAT REVEAL HYPERVARIABLE RESTRICTION FRAGMENT LENGTH POLYMORPHISMS WITHIN THE ABR GENE

1. INTRODUCTION

The present invention relates to nucleic acid molecules which comprise subfragments of the ABR gene. It is based, in part, on the discovery that the nucleic acid molecules of the invention may be used to demonstrate restriction fragment length polymorphism among individuals.

2. BACKGROUND OF THE INVENTION

The human BCR gene on chromosome 22 is specifically involved in the Philadelphia translocation, t(9; 22), a chromosome rearrangement present in the leukemic cells of patients with chronic myeloid leukemia (CML) or acute lymphoblastic leukemia (ALL). In most cases, the breakpoints on chromosome 22 are found within a 5.8 kb region of DNA designated the major breakpoint cluster region (Mbcr) of the BCR gene. Hybridization experiments have indicated that the human genome contains sequences related to the BCR gene. Heisterkamp et al. (1989, Nucl. Acids Res. 17: 8821-8831) have reported the cloning of one of these BCR-related sequences, termed ABR, located on chromosome 17p. ABR was reported (Id.) to be a functionally active gene containing exons very similar to those found within the Mbcr. ABR was also found (Id.) to exhibit great genomic variability associated with two different variable tandem repeat (VTR) regions located within two introns.

ABR appears to contain five small exons with a deduced amino acid sequence very similar to exons 1-5 of the Mbcr. ABR and BCR differ dramatically in one aspect: the BCR gene, although specifically involved in chromosomal translocations, was not particularly difficult to clone and does not appear to be genetically unstable. The gene has not been observed to vary in length among DNA samples from normal individuals, except for a polymorphism in the first intron (Rubin et al., 1988, Nucl. Acids Res. 16: 8741). In contrast, cloned segments of the ABR gene have been found to be highly unstable when propagated in *E. coli*, and a large number of different-sized alleles were found to exist in the general human population.

The variable tandem repeat regions, termed VTR-A and VTR-B, are located in ABR introns. VTR-A, within an intron 5' to the Mbcr homologous exons, appears to be the largest source of variability. VTR-B is located between Mbcr homologous exons 3 and 4. Interestingly, the location of this VTR corresponds to the Mbcr region highly prone to rearrangement in CML. Hybridization of a VTR-B probe to blots containing the cloned Mbcr region has failed to detect homologous regions.

Hypervariable regions have been described previously, either alone or in association with genes and the VTR regions described above fit the general patterns. For example, hypervariable regions consisting of 36, 14 and 17 bp tandem arrays have been found as interzeta, zeta-intron and alpha-globin 3 repeats (Goodbourn et al., 1983, Proc. Natl. Acad. Sci. U.S.A. 80: 5022-5026; Proudfoot et al, 1982, Cell 31:533-563; Jarman et al., 1986, EMBO J. 5: 1857-1863). Minisatellites from the insulin and Ha-rasl loci (Bell et al., 1982, Nature 295: 31-35, Capon et al., 1983, Nature 302: 33-37) have also been characterized and they can be used as chromosome-specific single copy probes. Abnormally high rates of genetic exchange have been observed in vivo and in vitro and it has been suggested that VTRs may promote such recombination events (Jeffreys et al., 1985, Nature 314: 67-73). They may operate as enhancer elements or in the organization of chromosome structure.

3. SUMMARY OF THE INVENTION

The present invention relates to nucleic acid molecules which comprise subfragments of ABR gene sequence. In particular embodiments, the nucleic acid molecules of the invention comprise portions of nucleic acid sequence contained in plasmids pVNTR-A or pVNTR-B. The invention is based, in part, on the discovery that a Taq-1 fragment of pVNTR-B, an EcoRI/HindIII fragment of pVNTR-A and, in preferred embodiments, a combination of these two fragments may be used to demonstrate restriction fragment length polymorphisms in the DNA of human subjects. Such restriction fragment length polymorphisms may provide a "genetic fingerprint" which may be used to identify individual persons or to provide evidence of a filial relationship in paternity cases. The nucleic acid sequences of the invention offer the advantage of producing an easily readable pattern in restriction fragment polymorphism analysis.

4. DESCRIPTION OF THE FIGURES

FIG. 1. Restriction enzyme map of the ABR Locus. The location of the probes used in this study are indicated above the restriction enzyme map with hatched boxes. Boxed areas in the map delineate the approximate position of exons; Mbcr-homologous exons 1-5 are noted with vertical arrows beneath the map. The approximate locations of the variable tandem repeats A and B are indicated with horizontal arrows. Restriction enzymes used include B=Bam HI, Bg=Bgl II, Bs=Bst EII, E=Eco RI, H=Hind III, S=Sst I.

Figure 2:
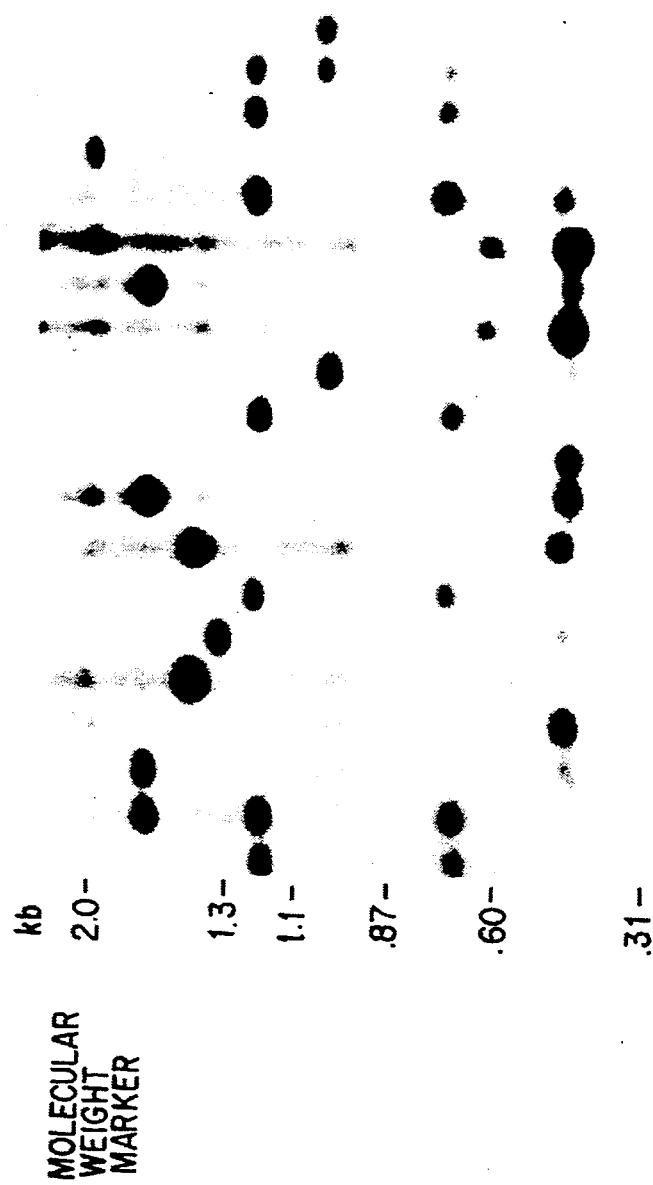

FIG. 2. Restriction fragment length polymorphism analysis of a panel of genomic DNAs digested with TaqI subjected to Southern blotting, hybridization to the 0.7 kb radiolabelled pVNTR-B TaqI fragment probe, and autoradiography.

Figure 3:
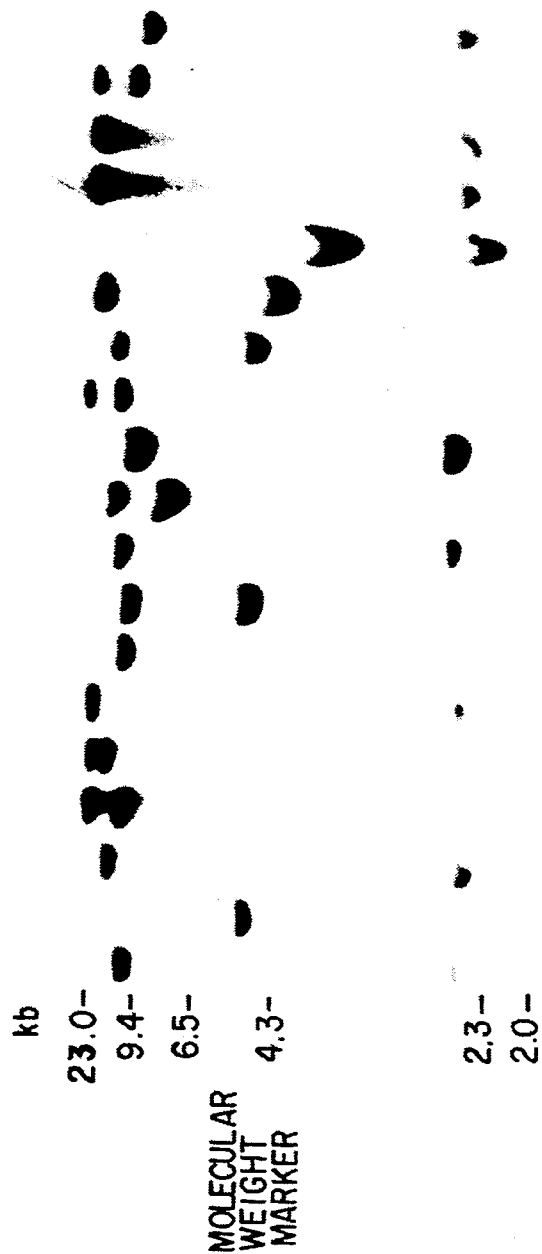

FIG. 3. Restriction fragment length polymorphism analysis of a panel of genomic DNAs digested with TaqI, subjected to Southern blotting, hybridization to radiolabelled pVNTR-A probe, and autoradiography.

5. DETAILED DESCRIPTION OF THE INVENTION

The present invention relates to nucleic acid molecules which comprise subfragments of ABR gene sequence. In particular embodiments, the nucleic acid molecules comprise portions of nucleic acid sequence contained in plasmids pVNTR-A or pVNTR-B or nucleic acid molecules having substantially similar sequences. Substantially similar sequences, as defined herein, are sequences which are at least 75 percent identical. VNTR-B represents a subcloned fragment from the ABR gene, and is described in Heisterkamp et al. (1989, Nucleic Acids Research, which is incorporated by reference in its entirety herein). A restriction map of the ABR locus which shows the relative positions of VNTR-A and VNTR-B, is depicted in FIG. 1. VNTR- A is located approximately 9 kb 5, of VNTR-B. Plasmid pVNTR-A contains an approximately 1.1 kb EcoRI/HindIII DNA fragment comprising VNTR-A inserted into pUC19 vector, and is deposited with the ATCC and assigned accession number 68409. Plasmid pVNTR-B contains an approximately 4.2 kb HindIII/EcoRI DNA fragment comprising VNTR-B inserted into pUC8 vector, and is deposited with the ATCC and assigned accession numbers 61534, for *E. coli* containing plasmid pVNTR-B, and 61535, for purified pVNTR-B plasmid DNA. The present invention provides for both pVNTR-A and pVNTR-B, as well as VNTR-A and VNTR-B fragments or subfragments derived therefrom, and DNA or RNA molecules corresponding to VNTR-A and VNTR-B sequence derived therefrom.

According to a preferred embodiment of the invention, an approximately 0.6 kb TaqI fragment may be prepared from plasmid pVNTR-B using TaqI restriction endonuclease and reaction conditions supplied by the TaqI manufacturer or in 100 mM NaCl, 10 mM Tris-HCL at pH 7.7, 10 mM $MgCl_2$, 1 mM DTT, and 100 μg/ml bovine serum albumin at a temperature of about 65° C. under paraffin oil, using techniques known in the art. The resulting 0.6 kb TaqI fragment may then be purified from other fragments using techniques known in the art, including, but not limited to, agarose and polyacrylamide gel electrophoresis. The resulting purified 0.6 kb TaqI fragment may then be labelled so as to provide a detectable label. Suitable labels include, but are not limited to, radioactive, fluorescent, chromophoric, or enzymatic labels. The purified, labelled 0.6 kb TaqI VNTR-B (hereinafter referred to as the VNTR-B probe) probe may then be used in restriction fragment length polymorphism (RFLP) analysis as described below.

According to another preferred embodiment of the invention, a VNTR-A probe may be prepared in which pVNTR-A may be detectably labelled (as described for the 0.6 kb TaqI fragment of pVNTR-B, supra) or the 1.1 kb EcoRI/HindIII insert of pVNTR-A, which comprises the VNTR-A locus, may be prepared, purified, and labelled. The 1.1 kb EcoRI/HindIII insert may be prepared using EcoRI and HindIII restriction endonucleases under reaction conditions specified by the enzyme manufacturer or in 50 mM NaCl, 100 mM Tris-HCl pH 7.5, 5 mM $MgCl_2$, and 100 μg/ml bovine serum albumin at about 37° C., using concentrations of enzyme and DNA substrate known to one skilled in the art.

In alternate embodiments of the invention, the 0.6 kb TaqI VNTR-B fragment or a VNTR-A fragment, or oligonucleotide fragments derived therefrom, may be utilized in polymerase chain reaction using genomic DNA as a template to produce DNA products for restriction fragment length polymorphism analysis. The polymerase chain reaction is a technique which is known to one skilled in the art and is described in Saiki et al. (1985, Science 230:1350–1354, which is incorporated by reference in its entirety herein). The amplification of sequences may be desirable in situations where a limited quantity of subject DNA is available.

In alternate embodiments, VNTR-A or VNTR-B probes may be labelled by nick-translation, primer extension, or by transcription into radiolabelled RNA molecules using techniques well known in the art.

VNTR-A and VNTR-B probes prepared according to the invention may then be utilized in RFLP analysis, a technique which allows the preparation of a "genetic fingerprint" which can reveal differences in the DNA sequences among individual subjects. In preferred embodiments of the invention, genomic DNA may be prepared from samples of cells or tissues obtained from individual subjects, such as human subjects. A particularly suitable source of genomic DNA is peripheral blood lymphocytes. High molecular weight DNA may be prepared according to methods set forth in Heisterkamp et al. (1983, J. Mol. Appl Genet. 2:57–68). The DNA may then be digested using restriction endonuclease(s) to produce restriction fragments which may then be separated electrophoretically and then blotted according to the method of Southern (1975, J. Mol. Biol. 98:503). The blotted fragments may then be hybridized to labelled VNTR-A and/or VNTR-B probes. In preferred embodiments of the invention, VNTR-A and VNTR-B probes are used together to produce a highly specific "genetic fingerprint." Preferred post-hybridization washing conditions are 0.3×SSC, 0.1% sodium dodecyl sulfate, and 0.1% sodium pyrophosphate at 65° C. In preferred embodiments of the invention, DNA for RFLP analysis may be cleaved with the enzyme TaqI prior to blotting and hybridization with VNTR-A and/or VNTR-B probes. With respect to VNTR-B probes, Hinf, like TaqI also cuts within the VNTR, and is suitable for RFLP analysis; the enzymes BamHI, BglII, BstEII, EcoRI, HindIII, and SstI appear to cut outside the VNTR generating one fragment per allele which may render it difficult to differentiate between different-sized alleles. With respect to VNTR-A probes, the enzymes BamHI, BglII, BstEII, EcoRI, HindIII and SstI also may be used to generate polymorphic bands.

Following hybridization and washing of the Southern Blots, the pattern of restriction fragments which have hybridized to detectably labelled VNTR-A and/or VNTR-B probe may then be analyzed using standard methods to identify restriction fragment length polymorphisms.

6. EXAMPLE: A HYPERVARIABLE RFLP WITHIN THE ABR GENE LOCATED AT 17p13.3

A 0.6 kb TaqI fragment was isolated from plasmid pVNTR-B and was used as a probe for hybridization with Southern blots carrying genomic DNAs from a variety of individuals. The genomic DNAs had been cleaved with TaqI restriction endonuclease. Following hybridization, the filters were washed at a stringency of 0.3×SSC. As shown in FIG. 2, TaqI was found to cut within the VNTR-B locus of the ABR gene, generating between about 1 and 4 different sized alleles per individual when hybridized with the 0.6 kb probe.

Conventional frequency calculations were not possible when the number of different sized fragments seen per individual is variable. Frequencies are given as the fraction of individuals in whom the band was present without regard to intensity. Calculations are based on DNAs from 49 unrelated individuals digested with TaqI. 2.05 kb=0.041, 1.75=0.16, 1.51=0.10, 1.35=0.061, 1.25=0.28, 1.05=0.12, 0.7=0.33, 0.67=0.14, 0.54=0.02, 0.47=0.84, 0.37=0.082 and 0.28 kb=0.041.

A heterozygosity of 78% was observed in 49 unrelated individuals.

7. EXAMPLE: VNTR-A, A SECOND HYPERVARIABLE RESTRICTION FRAGMENT LENGTH POLYMORPHISM WITHIN THE ABR GENE LOCATED AT 17p13.3

Radiolabelled VNTR-A probe was prepared and used as a probe for hybridization with Southern blots carrying TaqI digested genomic DNAs prepared from white blood cells of unrelated individuals. Post hybridization washings were performed in 0.15×SSC. As shown in FIG. 3, Taq was found to generate bands from 2.4 to 23 kb which were visible upon hybridization with VNTR-A probe.

The frequencies of the alleles were calculated on the TaqI digestion of DNAs from 51 unrelated individuals. 23 kb=0.186, 18=0.098, 10=0.088, 9.4=0.147, 9.2=0.039, 9.0=0.020, 7.0=0.020, 4.8=0.098, and 2.4=0.304. A heterozygosity of 88% was observed in these individuals for VNTR-A. The combined heterozygosity of VNTR-A and VNTR-B probes was found to be >99%.

8. EXAMPLE: THE USE OF VNTR-A AND VNTR-B IN DETERMINATION OF PATERNITY

The following example illustrates the use of VNTR-A and VNTR-B probes in pedigree analysis. Haplotype analysis at the phenylalanine hydroxylase (PAH) locus is currently used in the prenatal diagnosis of phenylketonuria (PKU). Haplotype analysis also indicates that less severe serum phenylalanine elevations result from mutation at the PAH locus. We reported a documented case of siblings with the same phenylalanine hydroxylase (PAH) genotype, similar phenylalanine loading study results, normal neopterin to biopterin ratios; but, different clinical manifestations of hyperphenylalaninemia (HP). The results suggest caution when using genetic analysis at the PAH locus to predict the clinical outcome of HPA.

Of the three siblings, the two eldest were born before newborn blood phenylalanine testing was routine. The eldest sibling, who was never on a phenylalanine restricted diet, is normal at age 35 years as evidenced by an IQ estimated at 130. The second sibling, the proband, was diagnosed at 13 months and despite an attempt at dietary therapy is severely retarded (IQ approximately 30). The youngest child was diagnosed neonatally and maintained on a phenylalanine restricted diet until age 6. The youngest child is now 25 with an IQ of 114. IQ measurements are based on the Wechsler Adult Intelligence Scale. A complete medical evaluation did not reveal any other clinical problems in the proband, suggesting mental retardation is the result of an abnormal phenylalanine level. All three siblings have elevated plasma phenylalanine. As adults their average blood phenylalanine levels range from 12-16 mg/dl on a normal diet. A natural protein challenge was conducted when the siblings were 17, 14.5, and 9 years of age. All three siblings show a pattern indicative of atypical PKU in that plasma phenylalanine levels rise moderately, peak at about 24 hours and return to their basal level after 72 hours.

Haplotype analysis was conducted using standard techniques (Blaskovics et al., J. Inter. Metab. Dis. 9:178-182). For this family the restriction enzyme MspI was completely informative while XmnI, BglII, PvuII, EcoRI, and EcoRV were partially informative; the data established that the three siblings had identical PAH phenotypes. As all eight polymorphic sites within the PAH gene are within 100 kb it is unlikely that a chromosomal crossover occurred. Moreover, the pattern of polymorphic sites is not indicative of a crossover event. Illegitimacy was tested using two probes that hybridize to regions containing VNTRs (variable number tandem repeats). The heterozygosity of VNTR-A is 78% and that of VNTR-B is 88%. Both probes suggest that this is a nuclear family. As the mother has normal phenylalanine levels, maternal PKU was not a problem. As normal neopterin/biopterin ratios indicate no involvement with dihydropteridine reductase or the enzymes involved in the synthesis of tetrahydrobiopterin from guanosine triphosphate, perhaps a subtle variation can explain the different phenylalanine toxicities found in this family. Kang et al. (1970, Pediatrics 45:83-93), working before PAH restriction fragment length polymorphisms were recognized, reported siblings with similar plasma phenylalanine levels but different developmental responses. In this study we have demonstrated that different clinical phenotypes for the identical PAH genotype can be found.

9. DEPOSIT OF MICROORGANISM

The following recombinant plasmids have been deposited with the American Type Culture Collection in Rockville, Md.:

| Plasmid | Accession Number |
| --- | --- |
| pVNTR-A | 68409 |
| pVNTR-B | 61534 (*E. coli* containing pVNTR-B plas.) |
|  | 61535 (purified pVNTR-B plasmid DNA) |

The present invention is not to be limited in scope by the specific embodiments described herein. Indeed, various modifications of the invention in addition to those described herein will become apparent to those skilled in the art from the foregoing description and accompanying figures. Such modifications are cited herein, the disclosures of which are incorporated by reference in their entireties.

What is claimed is:

1. An essentially purified and isolated nucleic acid fragment that is 1.1 kilobases in length and which comprises the VNTR-A region as contained in plasmid pVNTR-A, prepared from *Escherichia coli* deposited with the American Type Culture Collection and assigned accession number 68409.

2. A plasmid vector comprising the essentially purified and isolated nucleic acid fragment of claim 1.

3. Plasmid pVNTR-A, as prepared from *Escherichia coli* deposited with the American Type Culture Collection and assigned accession number 68409.

4. The essentially purified and isolated nucleic acid fragment of claim 1 which is detectably labeled.

5. An essentially isolated nucleic acid fragment that is 4.2 kilobases in length and which comprises the VNTR-B region, as contained in plasmid pVNTR-B, prepared from *Escherichia coli* deposited with the American Type Culture Collection and assigned accession number 61534.

6. A plasmid vector comprising the essentially purified and isolated nucleic acid of claim 5.

7. Plasmid pVNTR-B, as prepared from *Escherichia coli* deposited with the American Type Culture Collection and assigned accession number 61534.

8. An essentially purified and isolated 0.6 kilobase nucleic acid fragment prepared from the nucleic acid fragment of claim 5 or from the plasmid of claim 6 or 7 by a method that comprises digestion with the restriction endonuclease TaqI followed by purification of the 0.6 kb fragments.

9. A plasmid vector comprising essentially purified and isolated 0.6 kilobase TaqI fragment of claim 8.

10. The essentially purified and isolated nucleic acid fragment of claim 5 which is detectably labeled.

11. The essentaiily purified and isolated nucleic acid fragment of claim 8 which is detectably labeled.

12. A method of producing a genetic fingerprint comprising:
   (i) preparing and isolating genomic DNA from an individual;
   (ii) digesting the genomic DNA prepared in step (i) with at least one restriction endonuclease to produce restriction fragments;
   (iii) separating the restriction fragments electrophoretically;
   (iv) producing a Southern blot of separated fragments;
   (v) hybridizing the Southern blot produced in step (iv) to an essentially purified and isolated nucleic acid according to claim 1 that has been detectably labeled; and
   (vi) identifying restriction fragment length polymorphisms.

13. A method of producing a genetic fingerprint comprising:
   (i) preparing and isolating genomic DNA from an individual;
   (ii) digesting the genomic DNA prepared in step (i) with at least one restriction endonuclease to produce restriction fragments;
   (iii) separating the restriction fragments electrophoretically;
   (iv) producing a Southern blot of separated fragments;
   (v) hybridizing the Southern blot produced in step (iv) to an essentially purified and isolated nucleic acid according to claim 5 that has been detectably labeled; and
   (vi) identifying restriction fragment length polymorphisms.

14. A method of producing a genetic fingerprint comprising:
   (i) preparing and isolating genomic DNA from an individual;
   (ii) digesting the genomic DNA prepared in step (i) with at least one restriction endonuclease to produce restriction fragments;
   (iii) separating the restriction fragments electrophoretically;
   (iv) producing a Southern blot of separated fragments;
   (v) hybridizing the Southern blot produced in step (iv) to an essentially purified and isolated nucleic acid according to claim 8 that has been detectably labeled; and
   (vi) identifying restriction fragment length polymorphisms.

15. A method of producing a genetic fingerprint comprising:
   (i) preparing and isolating genomic DNA from an individual;
   (ii) digesting the genomic DNA prepared in step (i) with at least one restriction endonuclease to produce restriction fragments;
   (iii) separating the restriction fragments electrophoretically;
   (iv) producing a Southern blot of separated fragments;
   (v) hybridizing the Southern blot produced in step (iv) to a detectably labeled essentially purified and isolated nucleic acid fragment that is 1.1 kilobases in length and which comprises the VNTR-A region, as contained in plasmid pVNTR-A, prepared from *Escherichia coli* deposited with the American Type Culture Collection and assigned accession number 68409, and (b) the essentially purified and isolated nucleic acid fragment of claim 11; and
   (vi) identifying restriction fragment length polymorphisms.

* * * * *